US008202973B2

(12) United States Patent
Nicolaisen et al.

(10) Patent No.: US 8,202,973 B2
(45) Date of Patent: Jun. 19, 2012

(54) METHOD FOR THE PRODUCTION OF VITAMIN K-DEPENDENT PROTEINS

(75) Inventors: Else Marie Nicolaisen, Frederiksberg (DK); Lars Soegaard Nielsen, Niva (DK)

(73) Assignee: Novo Nordisk Health Care AG, Zurich (CH)

(*) Notice: Subject to any disclaimer, the term of this patent is extended or adjusted under 35 U.S.C. 154(b) by 2328 days.

(21) Appl. No.: 10/398,422

(22) PCT Filed: Oct. 2, 2001

(86) PCT No.: PCT/DK01/00635
§ 371 (c)(1),
(2), (4) Date: Sep. 2, 2003

(87) PCT Pub. No.: WO02/29045
PCT Pub. Date: Apr. 11, 2002

(65) Prior Publication Data
US 2004/0058413 A1    Mar. 25, 2004

Related U.S. Application Data

(60) Provisional application No. 60/238,944, filed on Oct. 10, 2000, provisional application No. 60/271,581, filed on Feb. 26, 2001, provisional application No. 60/276,322, filed on Mar. 16, 2001.

(30) Foreign Application Priority Data

Oct. 2, 2000   (DK) ................................ 2000 01456
Feb. 16, 2001  (DK) ................................ 2001 00262
Mar. 14, 2001  (DK) ................................ 2001 00430
May 14, 2001   (DK) ................................ 2001 00751

(51) Int. Cl.
*C07H 21/04* (2006.01)
*C12P 21/02* (2006.01)
*C07K 7/08* (2006.01)

(52) U.S. Cl. .................... 536/23.1; 435/325; 435/320.1; 435/69.1; 530/380

(58) Field of Classification Search ................. 536/23.1; 435/320.1, 325, 69.1; 530/380
See application file for complete search history.

(56) References Cited

U.S. PATENT DOCUMENTS

| 4,784,950 A |   | 11/1988 | Hagen et al. |        |
|-------------|---|---------|--------------|--------|
| 5,460,950 A | * | 10/1995 | Barr et al.  | 435/69.1 |
| 5,789,203 A | * | 8/1998  | Chapman et al. | 435/69.6 |
| 5,965,789 A | * | 10/1999 | Lubon et al. | 800/14 |

FOREIGN PATENT DOCUMENTS

| JP | 1993-508551    |   | 7/1990 |
| WO | WO 88/03926    | * | 6/1988 |
| WO | WO 88/03926 A1 |   | 6/1988 |
| WO | WO 92/01795    |   | 2/1992 |
| WO | WO 92/01795 A1 |   | 2/1992 |
| WO | WO 92/15686    |   | 9/1992 |
| WO | WO 92/15686 A1 |   | 9/1992 |
| WO | WO 92/19636    |   | 11/1992 |
| WO | WO 92/19636 A1 |   | 11/1992 |
| WO | WO 00/54787    |   | 9/2000 |
| WO | WO 00/54787 A1 |   | 9/2000 |

OTHER PUBLICATIONS

Benton et al. Multi-Site-Specificity of the Vitamin K-Dependent Carboxylase: In Vitro Carboxylation of des-gamma-carboxylated Bone Gla Protein and Des-gamma-carboxylated Pro Bone Gla Protein. 1995, Biochemistry vol. 34, pp. 9541-9551.*
Camire et al. Enhanced gamma Carboxylation of Recombinant Factor X Using a Chimeric Construct Containing the Prothrombin Propeptide. 2000, Biochemistry vol. 39, pp. 14322-14329.*
Stanley et al. The Propeptides of the Vitamin K dependent Proteins Possess Different Affinities for the Vitamin K dependent Carboxylase. 1999, J. Biol. Chem. vol. 274, No. 24, pp. 16940-16944.*
Berkner, The Journal of Nutrition, vol. 130, No. 8, pp. 1877-1880 (2000).
Furie et al., Annals of the New York Academy of Sciences, vol. 614, pp. 1-10 (1991).
Furie et al., Blood, vol. 93, No. 6, pp. 1798-1808 (1999).
Knobloch et al., The Journal of Biological Chemistry, vol. 262, No. 32, pp. 15334-15337 (1987).
Li et al., Biochemistry, vol. 36, No. 21, pp. 6384-6390 (1997).
Rehemtulla et al., Proc. Natl. Acad. Sci. USA, vol. 90, No. 10, pp. 4611-4615 (1993).
Sugiura et al., Proc. Natl. Acad. Sci. USA, vol. 94, No. 17, pp. 9069-9074 (1997).
Wu et al., Science, vol. 254, pp. 1634-1636 (1991).
Zhang et al., Blood, vol. 84, No. 1, pp. 169-175 (1994).
Sugiura, I et al., Proceedings of the National Academy of Sciences of the USA, 1997, vol. 94, Part 17, pp. 9069-9074.
Rehemtulla, A et al., Proceedings of the National Academy of Sciences of the USA, 1993, vol. 90, Part 10, pp. 4611-4615.
Zhang, P et al., Blood, 1994, vol. 84, Part 1, pp. 169-175.
Li, S et al, Biochemistry, 1997, vol. 36, Part 21, pp. 6384-6390.
Knobloch J E et al., Journal of Biological Chemistry, 1987, vol. 262, Part 32, pp. 15334-15337.
Furie B et al., Annals of the New York Academy of Sciences, 1991, vol. 614, pp. 1-10.
Furie B et al., Blood, 1999, vol. 93, Part 6, pp. 1798-1808.
Berkner K.L, The Journal of Nutrition, 2000, vol. 130, Part 8, pp. 1877-1880.
Wu, Sheue-Mei et al., Science, 1991, vol. 254, pp. 1634-1635.
Benton et al., Biochemistry, 1995, vol. 34, pp. 9541-9551.

(Continued)

*Primary Examiner* — Chih-Min Kam
(74) *Attorney, Agent, or Firm* — Rosemarie R. Wilk-Orescan

(57) ABSTRACT

The present invention relates to a novel method for preparing vitamin K-dependent proteins. Furthermore the present invention relates to novel co-transfected eucaryotic host cells and recombinant vectors to be used in this improved method for preparing vitamin K-dependent proteins.

69 Claims, 3 Drawing Sheets

OTHER PUBLICATIONS

Rodney Camire et al., Biochemistry, 2000. vol. 39, Part 46, pp. 14322-14329.

Thomas B. Stanley et al., Journal of Biological Chemistry, 1999, vol. 274, Part 24, pp. 16940-16944.

Stanley, Thomas B. et al., Biochemistry, 1999, vol. 38, pp. 15681-15687.

Chen, L. et al., Oncogene, 1990, vol. 5, Part 9, pp. 1391-1395.

* cited by examiner

Comparison of FVII expressing CHO-K1 cells (Control) and cells coexpressing FVII and a free FVII propeptide (FVII pro-peptide). Results are shown in pg FVII expression per cell per day.

METHOD FOR THE PRODUCTION OF VITAMIN K-DEPENDENT PROTEINS

CROSS-REFERENCE TO RELATED APPLICATIONS

This application is a 371 of PCT/DK01/00635 filed Oct. 2, 2001, which claims priority of U.S. provisional application No. 60/238,944 filed on Oct. 10, 2000; U.S. provisional application No. 60/271,581 filed on Feb. 26, 2001; and U.S. provisional application No. 60/276,322 filed on Mar. 16, 2001; and which also claims priority under 35 U.S.C. 119 of Danish application no. PA 2000 01456 filed on Oct. 2, 2000; Danish application no. PA 2001 00262 filed on Feb. 16, 2001; Danish application no. PA 2001 00430 filed on Mar. 14, 2001; and Danish application no. PA 2001 00751 filed on May 14, 2001, the contents of which are fully incorporated herein by reference.

FIELD OF THE INVENTION

The present invention relates to a novel method for preparing vitamin K-dependent proteins and in particular coagulation factor VII (FVII). Furthermore the present invention relates to novel co-transfected eucaryotic host cells and recombinant vectors to be used in this improved method for preparing vitamin K-dependent proteins.

BACKGROUND OF THE INVENTION

The biosynthesis of vitamin K-dependent proteins includes several posttranslational processing steps before a mature functional protein is obtained.

Vitamin K is a necessary cofactor for the gamma-carboxylation of glutamic acid residues in these vitamin K-dependent proteins, including the procoagulant factors thrombin, factor VII, IX, and X; the anticoagulants protein C and protein S; and other proteins such as osteocalcin (bone Gla protein), matrix Gla protein, and proline-rich Gla protein 1. This carboxylation is required for normal hemostasis, because it enables calcium binding and attachment of the procoagulants and anticoagulants to phospholipids.

Gamma-glutamyl carboxylase is an integral membrane microsomal enzyme located in the rough endoplasmic reticulum. It carboxylates glutamate residues located in the Gla domain of the vitamin K-dependent proteins. Human gamma-glutamyl carboxylase cDNA has recently been isolated and sequenced (Wu S M et al. Science 254:1634, 1991). Studies of the biosynthesis of Vitamin K-dependent proteins in BHK and CHO cells, show that the carboxylase is present in both the endoplasmatic reticulum (ER) and the Golgi complex, and that the propeptide, containing the carboxylase recognition site is cleaved after completion of the gamma-carboxylation.

It has been speculated whether the propeptide can stimulate the carboxylase activity (Sigiura, I. et al. (1997) Proc. Natl. Acad. Sci., 9, 9069-9074, Knobloch and Suttie (1987) J. Biol. Chem. 262, 15334-15337, Furie et al (1999) Blood, 93, 1798-1808).

Blood coagulation is a process consisting of a complex interaction of various blood components, or factors, which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors that have undergone such a conversion and generally referred to as "active factors," and are designated by the addition of a lower case "a" suffix (e.g., activated factor VII (FVIIa)).

Activated factor X (FXa) is required to convert prothrombin to thrombin, which then converts fibrinogen to fibrin as a final stage in forming a fibrin clot. There are two systems, or pathways, that promote the activation of FX. The "intrinsic pathway" refers to those reactions that lead to thrombin formation through utilization of factors present only in plasma. A series of protease-mediated activations ultimately generates factor IXa which, in conjunction with factor VIIIa, cleaves FX into FXa. A similar proteolysis is effected by FVIIa and its co-factor, tissue factor, in the "extrinsic pathway" of blood coagulation. Tissue factor is a membrane bound protein and does not normally circulate in plasma. Upon vessel disruption, however, it can complex with FVIIa to catalyze FX activation or factor IX activation in the presence of Ca++ and phospholipid. While the relative importance of the two coagulation pathways in hemostasis is unclear, in recent years FVII and tissue factor have been found to play a pivotal role in the regulation of blood coagulation.

FVII is a trace plasma glycoprotein that circulates in blood as a single-chain zymogen. The zymogen is clot inactive. Single-chain FVII may be converted to two-chain FVIIa by FXa, factor XIIa, factor IXa or thrombin in vitro. FXa is believed to be the major physiological activator of FVII. Like several other plasma proteins involved in hemostasis, FVII is dependent on vitamin K for its biosynthesis, which is required for the gamma-carboxylation of 10 glutamic acid residues in the amino terminus of the protein. The intracellular post-translational processing of FVII takes place in the endoplasmatic reticulum (ER) and the Golgi complex. Besides the vitamin K-dependent gamma-carboxylation, FVII is subjected to limited proteolysis to remove the N-terminal propeptide, and glycosylation of asparagine-145 and -322, and serine-52 and -60 (FIG. 1).

The gamma-carboxylated glutamic acid (Gla) residues are required for the metal-associated interaction of FVII with phospholipids.

In the presence of tissue factor, phospholipids and calcium ions, the two-chain FVIIa rapidly activates FX or factor IX by limited proteolysis.

Protein C is a serine protease and naturally occurring anticoagulant that plays a role in the regulation of homeostasis by inactivating factors Va and VIIIa in the coagulation cascade. Human protein C is made in vivo primarily in the liver as a single polypeptide of 461 amino acids. This single chain precursor molecule undergoes multiple post-translational modifications including carboxylation of nine glutamic acid residues, resulting in nine Gla residues.

Protein S also exhibits anticoagulant activity in in vitro clotting assays. Protein S demonstrates anticoagulant cofactor activity for activated protein C. Protein S has also been shown to be an anticoagulant factor in the absence of activated protein C as it can inhibit prothrombinase activity in assays free of activated protein C and binds to Factor Va or Factor Xa and functions as an anticoagulant without activated protein C. Protein S is physiologically a very important antithrombotic factor since hereditary or acquired deficiencies of protein S are associated with venous and arterial thrombotic disease. A deficiency of free protein S with a normal level of total protein S has been described in some patients with thrombotic disease.

It is often necessary to selectively block the coagulation cascade in a patient. Anti-coagulants such as protein C or protein S may be used, for example, during kidney dialysis, or to treat deep vein thrombosis, disseminated intravascular coagulation (DIC), a patient at risk for acute thrombosis, protein S deficiency, sepsis, inflammation, cancer, patients undergoing surgery and a host of other medical disorders.

Osteocalcin is composed of 49 amino acid residues which include three Gla residues. The function of this protein is thought to be to suppress excessive mineralization. Osteocalcin is a bone-specific protein that is secreted by osteoblasts. A fraction of newly synthesized osteocalcin is released into the bloodstream, where its concentration correlates with the indices of osteoblastic activity and bone formation rate. In humans, changes in circulating osteocalcin levels have been associated with metabolic bone diseases such as osteoporosis and hyperparathyroidism.

Matrix Gla Protein (MGP) is composed of 79 amino acids including 5 Gla residues. This protein is usually found in demineralized matrix and believed to have a certain function in the initiation of bone formation.

There is still a need in the art for improved systems for the production of recombinant vitamin K-dependent proteins and particular recombinant coagulation factors. The present invention fulfills this need by providing a method that gives a more efficient, faster production and/or higher yield of recombinant vitamin K-dependent proteins, in particular FVII.

DESCRIPTION OF THE INVENTION

The present invention relates to a novel method for preparing vitamin K-dependent proteins and in particular coagulation factor VII (FVII).

The N-terminal processing steps and in particular the gamma-carboxylation of glutamic acid residues of vitamin K-dendent proteins have been shown to be the limiting steps in the biosynthesis of these proteins, as exemplified with FVII by the present inventors. A method for increasing the gamma-carboxylation have been shown to increase the expression of recombinant vitamin K-dependent proteins.

The propeptide of the vitamin K-dendent proteins is essential for binding to the carboxylase, and it has to be covalently attached to the vitamin K-dependent protein in order for the Glu residues, in what will become the N-terminal of the later mature protein, to be carboxylated. We hypothesize that the free propeptide functions as an allosteric regulating molecule in the sense that when the concentration of free propeptide increases the activity of the gamma-carboxylation process also increases.

A direct increase in the concentration of free propeptides can be obtained by co-expression of free propeptide(s) per se. This can be done by transfection with the polynucleotide encoding free propeptide(s) with or without mutations and truncations, in one or more copies, and co-express this together with a polynucleotide encoding the vitamin K-dependent protein. The latter might contain another propeptide sequence, than that normally associated with the vitamin K-dependent protein. Expression of a polynucleotide encoding the vitamin K-dependent protein can be obtained either by transfecting the gene of interest into a cell or by activating (i.e., turning on) an endogenous gene encoding the vitamin K-dependent protein already present in primary, secondary, or immortalized cells of vertebrate origin, which is normally not expressed in the cells or is not expressed at physiologically significant levels in the cells as obtained. For activating genes of interest, homologous recombination can be used to replace or disable the regulatory region normally associated with the gene in cells as obtained with a regulatory sequence which causes the gene to be expressed at levels higher than evident in the corresponding nontransfected cell, or to display a pattern of regulation or induction that is different than evident in the corresponding nontransfected cell.

In a first aspect, the invention relates to a eucaryotic host cell expressing a first polynucleotide encoding a first propeptide and FVII or variants thereof in a first expression unit and expressing a second polynucleotide encoding a second free propeptide in a second expression unit. It is to be understood that the first polynucleotide is located in a first expression unit and that the second polynucleotide is located in a second expression unit, wherein the first and second expression units are different.

In second aspect, the invention relates to a eucaryotic host cell transfected with a first polynucleotide encoding a first propeptide and FVII or variants thereof in a first expression unit and transfected with a second polynucleotide encoding a second free propeptide in a second expression unit. It is to be understood that the first polynucleotide is located in a first expression unit and that the second polynucleotide is located in a second expression unit, wherein the first and second expression units are different. The actual order of transfection is off course trivial and thus, the host cell may be transfected first with the second polynucleotide or vice versa. The use of the terms "first propeptide" and "second propeptide" are merely out of convenience, thus the first and second propeptide may be the same or different.

The term "a eucaryotic host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (.g., ATCC CRL 1650), baby hamster kidney (BHK) and HEK293 (e.g., ATCC CRL 1573; Graham et al., *J. Gen. Virol.* 36:59-72, 1977) cell lines.

A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216-4220, 1980). Also useful are 3T3 cells, Namalwa cells, myelomas and fusions of myelomas with other cells.

The term "a polynucleotide" denotes a single- or double-stranded polymer of deoxy-ribonucleotide or ribonucleotide bases read from the 5' to the 3' end. Polynucleotides include RNA and DNA, and may be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term "nucleotides" is used for both single- and double-stranded molecules where the context permits. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

The term "a propeptide", as used herein, represent any amino acid sequence, which can bind a gamma-glutamyl carboxylase. Typical propeptides that directs a gamma-carboxylation of vitamin K-dependent proteins, are found at the N-terminal of a vitamin K-dependent protein and serves as a docking site or recognition sequence for interaction with gamma-glutamyl carboxylase, which carboxylates glutamate residues usually located in the Gla domain of vitamin K-dependent proteins. There may be more than one binding sites for the gamma-glutamyl carboxylase, e.i. gamma-glutamyl carboxylase recognition sequence, in one propeptide. One example of a propeptide within this definition is thus the natural propeptide sequence of FVII. Another example within this definition is the natural propeptide sequence of FVII connected to the natural propeptide sequence of factor IX within the same amino acid sequence.

The term "free propeptide", as used herein, is intended to m an a propeptide which is not connected to a vitamin K-dependent protein to be gamma-carboxylated. An example of a free propeptide is thus the propeptide of FVII without being connected to the amino acid sequence of FVII.

The terms "factor VII", or "FVII as used herein means a product consisting of the unactivated form (factor VII). The term "factor VIIa", or "FVIIa" as used herein means a product consisting of the activated form (factor VIIa). This includes proteins that have the amino acid sequence 1-406 of native human factor FVII or FVIIa. It also includes proteins with a slightly modified amino acid sequence, for instance, a modified N-terminal end including N-terminal amino acid deletions or additions so long as those proteins substantially retain the activity of FVIIa. "FVII" or "FVIIa" within the above definition also includes natural allelic variations that may exist and occur from one individual to another. Also, degree and location of glycosylation or other post-translation modifications may vary depending on the chosen host cells and the nature of the host cellular environment.

The term "variants", as used herein, is intended to designate FVII wherein one or more amino acid residues of the parent protein have been substituted by another amino acid residue and/or wherein one or more amino acid residues of the parent protein have been deleted and/or wherein one or more amino acid residues have been added to the parent protein. Such addition can take place either at the N-terminal end or at the C-terminal end of the parent protein or both.

The term "an expression unit", as used herein, means a polynucleotide comprising the following operably linked elements: (a) a transcription promoter; (b) a polynucleotide sequence encoding an amino acid sequence; and (c) a transcription terminator. An example of an expression unit is thus a DNA vector comprising the following linked elements: (a) a transcription promoter, (b) a cDNA sequence encoding a free propeptide; and (c) a transcription terminator.

The term "a vector", as used herein, means any nucleic acid entity capable of the amplification in a host cell. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contains a replication origin and at least one selectable gene, i.e., a gene which encodes a product which is readily detectable or the presence of which is essential for cell growth.

The term "a promoter" denotes a portion of a gene containing DNA sequences that provide for the binding of RNA polymerase and initiation of transcription. Promoter sequences are commonly, but not always, found in the 5' non-coding regions of genes.

In a third aspect, the invention relates to a eucaryotic host cell expressing a first polynucleotide encoding a first propeptide and a vitamin K-dependent protein in a first expression unit and expressing a second polynucleotide encoding a second free propeptide in a second expression unit.

In further aspect, the invention relates to a eucaryotic host cell transfected with a first polynucleotide encoding a first propeptide and a vitamin K-dependent protein in a first expression unit and transfected with a second polynucleotide encoding a second free propeptide in a second expression unit.

The term "a vitamin K-dependent protein", as used herein, means any protein, that is gamma-carboxylated on glutamic acid residues. Typical vitamin K-dependent proteins includes but are not limited to the procoagulant factors thrombin, factor VII, IX, and X; the anticoagulants protein C and protein S; and other proteins such as osteocalcin (bone Gla protein), matrix Gla protein, and proline-rich Gla protein 1.

In a further aspect the invention relates to a method for producing FVII or variants thereof comprising a) expression in a eucaryotic cell of a first polynucleotide encoding a first propeptide and FVII or variants thereof in a first expression unit and expression of a second polynucleotide encoding a second free propeptide in a second expression unit to produce a co-expressing eucaryotic host cell; b) cultivation in a suitable culture medium of the co-expressing eucaryotic host cell under conditions which allow the first polynucleotide and the second polynucleotide to be expressed.

In a further aspect the invention relates to a method for producing FVII or variants thereof comprising a) expression in a eucaryotic cell of a first polynucleotide encoding a first propeptide and FVII or variants thereof in a first expression unit and expression of a second polynucleotide encoding a second free propeptide in a second expression unit to produce a co-expressing eucaryotic host cell; b) cultivation in a suitable culture medium of the co-expressing eucaryotic host cell under conditions which allow the first polynucleotide and the second polynucleotide to be expressed; and c) isolation of FVII or variants thereof from the medium.

In a further aspect the invention relates to a method for producing FVII or variants thereof comprising a) transfection of a eucaryotic host cell with a first polynucleotide encoding a first propeptide and FVII or variants thereof in a first expression unit and transfection with a second polynucleotide encoding a second fre propeptide in a second expression unit to produce a co-transfected eucaryotic host cell; b) cultivation in a suitable culture medium of the co-transfected eucaryotic host cell under conditions which allow the first polynucleotide and the second polynucleotide to be expressed.

In a further aspect the invention relates to a method for producing FVII or variants thereof comprising a) transfection of a eucaryotic host cell with a first polynucleotide encoding a first propeptide and FVII or variants thereof in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotide and the second polynucleotide to be expressed; and c) isolation of FVII or variants thereof from the medium.

In a further aspect the invention relates to a method for producing FVIIa or variants thereof comprising a) transfection of a eucaryotic host cell with a first polynucleotide encoding a first propeptide and FVII or variants thereof in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotide and the second polynucleotide to be expressed; and c) isolation and activation of FVII or variants thereof from the medium.

In a further aspect the invention relates to a recombinant vector, wherein said vector comprises a polynucleotide encoding a free propeptide in an expression unit. The embodiments described below in respect of the second polynucleotide, the second free propeptide, and the second expression unit are individually or in combination also intended to represent embodiments of the polynucleotide, the free propeptide, and the expression unit encompassed within the recombinant vector.

In a further aspect the invention relates to a recombinant vector, wherein said vector comprises a first polynucleotide encoding a first propeptide and FVII or variants thereof in a first expression unit and a second polynucleotide encoding a second free propeptide in a second expression unit.

In a further aspect the invention relates to a recombinant vector, wherein said vector comprises a first polynucleotide encoding a first propeptide and a vitamin K-dependent protein in a first expression unit and a second polynucleotide encoding a second free propeptide in a second expression unit.

In a further aspect the invention relates to a method for preparing a eucaryotic host cell producing FVII comprising a) gene activating in a eucaryotic host cell a first polynucleotide encoding the amino acid sequence −18 to 406 of FVII and its propeptide in a first expression unit and b) transfection with a second polynucleotide encoding a second free propeptide in a second expression unit. In this respect, the amino acid sequence −18 to −1 is identical to the propeptide of FVII identified as SEQ ID NO:7.

In a further aspect the invention relates to a method for preparing a eucaryotic host cell producing FVII or variants thereof comprising a) transfection of a eucaryotic host cell with a first polynucleotide encoding a first propeptide and FVII or variants thereof in a first expression unit and b) transfection with a second polynucleotide encoding a second free propeptide in a second expression unit.

In a further aspect the invention relates to a method for producing a vitamin K-dependent protein comprising a) expression in a eucaryotic host cell of a first polynucleotide encoding a first propeptide and a vitamin K-dependent protein in a first expression unit and expression of a second polynucleotide encoding a second free propeptide in a second expression unit to produce a co-expressing eucaryotic host cell; b) cultivation in a suitable culture medium of the co-expressing eucaryotic host cell under conditions which allow the first polynucleotides and the second polynucleotide to be expressed.

In a further aspect the invention relates to a method for producing a vitamin K-dependent protein comprising a) expression in a eucaryotic host cell of a first polynucleotide encoding a first propeptide and a vitamin K-dependent protein in a first expression unit and expression of a second polynucleotide encoding a second free propeptide in a second expression unit to produce a co-expressing eucaryotic host cell; b) cultivation in a suitable culture medium of the co-expressing eucaryotic host cell under conditions which allow the first polynucleotides and the second polynucleotide to be expressed; and c) isolation of the vitamin K-dependent protein from the medium.

In a further aspect the invention relates to a method for producing a vitamin K-dependent protein comprising a) transfection of a eucaryotic host cell with a first polynucleotide encoding a first propeptide and a vitamin K-dependent protein in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotides and the second polynucleotide to be expressed.

In a further aspect the invention relates to a method for producing a vitamin K-dependent protein comprising a) transfection of a eucaryotic host cell with a first polynucleotide encoding a first propeptide and a vitamin K-dependent protein in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotides and the second polynucleotide to be expressed; and c) isolation of the vitamin K-dependent protein from the medium.

In a further aspect the invention relates to recombinant FVII or variants thereof obtainable by a method comprising a) transfection of a eucaryotic host cell with a first polynucleotide encoding a first propeptid and FVII or variants thereof in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotide and the second polynucleotide to be expressed.

In a further aspect the invention relates to recombinant FVII or variants thereof obtainable by a method comprising a) transfection of a eucaryotic host cell with a first polynucleotide encoding a first propeptide and FVII or variants thereof in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotide and the second polynucleotide to be expressed; and c) isolation of FVII or variants thereof from the medium.

In a further aspect the invention relates to recombinant FVIIa or variants thereof obtainable by a method comprising a) transfection of a eucaryotic host cell with a first polynucleotide encoding a first propeptide and FVII or variants thereof in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotide and the second polynucleotide to be expressed; and c) isolation and activation of FVII or variants thereof from the medium.

In a further aspect the invention relates to recombinant vitamin K-dependent protein obtainable by a method comprising a) transfection of a eucaryotic host cell with a first polynucleotide encoding a first propeptide and a vitamin K-dependent protein in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotides and the second polynucleotide to be expressed.

In a further aspect the invention relates to recombinant vitamin K-dependent protein obtainable by a method comprising a) transfection of a eucaryotic host cell with a first polynucleotide encoding a first propeptide and a vitamin K-dependent protein in a first expression unit and transfection with a second polynucleotide encoding a second free propeptide in a second expression unit to produce a co-transfected eucaryotic host cell; b) cultivation in a suitable culture medium of the co-transfected eucaryotic host cell under conditions which allow the first polynucleotides and the second polynucleotide to be expressed; and c) isolation of the vitamin K-dependent protein from the medium.

The first propeptide may be that propeptide normally associated with the vitamin K-dependent protein or it may be any other propeptide, such as a propeptide normally associated with a different vitamin K-dependent protein.

In one embodiment the first propeptide comprises one binding sequence for the gamma-glutamyl carboxylase. In another embodiment the first propeptide comprises two or more binding sequences for the gamma-glutamyl carboxylase. An example of the first propeptide is thus the propeptides normally associated with FVII and prothrombin covalently attached in the same expression unit.

In a further embodiment the second free propeptide comprises one binding sequence for the gamma-glutamyl carboxylase. In a further embodiment the second free propeptide comprises two or more binding sequences for the gamma-glutamyl carboxylase. An example of the second free propeptide is thus the propeptides normally associated with FVII and prothrombin covalently attached in the same expression unit.

In a further embodiment of the invention, the eucaryotic host cell is expressing a first polynucleotide encoding a first propeptide and FVII in a first expression unit and expressing a second polynucleotide encoding a second free propeptide in a second expression unit. In a particular embodiment the FVII is human FVII.

In a further embodiment of the invention, the eucaryotic host cell is transfected with a first polynucleotide encoding a first propeptide and FVII in a first expression unit and transfected with a second polynucleotide encoding a second free propeptide in a second expression unit. In a particular embodiment the FVII is human FVII.

In a further embodiment of the invention, the vitamin K-dependent protein is independently selected from prothrombin, factor IX, FVII, factor X, protein C, protein S, osteocalcin, proline-rich Gla protein 1 or matrix Gla protein. It should be understood that any one of these proteins constitutes an alternative embodiment of the invention.

In a further embodiment of the invention the eucaryotic host cell is further transfected with a polynucleotide encoding a gamma-glutamyl carboxylase in an expression unit. This expression unit may be an expression unit different from the first or second expression unit or the polynucleotide encoding the gamma-glutamyl carboxylase may be located in the first or second expression unit. Examples of gamma-glutamyl carboxylases are selected from recombinant human, rat, drosophila, mus musculus or hamster gamma-glutamyl carboxylases.

In a further embodiment of the invention the first propeptide comprises an amino acid sequence of the formula:

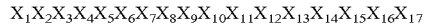

Wherein $X_1$, $X_4$, $X_5$, $X_6$, $X_7$, $X_9$, $X_{10}$ and $X_{13}$, are independently selected from
G, P, A, V, L, I, M, C, F, Y, W, H, K, R, Q, N, E, D, S, and T
and wherein $X_2$, $X_3$, $X_{11}$ and $X_{12}$ are independently selected from
V, L, P, N, A, I, S, F, M, W, Q, T, and Y
and wherein $X_6$ is independently selected from
G, and A
and wherein $X_{14}$, $X_{15}$, $X_{16}$ and $X_{17}$ are independently selected from
R, H, A, T, W, L, I, V, Q, K, Y, P, or is absent.

In one embodiment of the first propeptide $X_1$ is selected from A, S, N, R, T, and H.

In a further embodiment of the first propeptide $X_2$ is selected from V, L, P, N, and A.

In a further embodiment of the first propeptide $X_3$ is selected from L, I, V, and S.

In a further embodiment of the first propeptide $X_4$ is selected from S, R, N, T, D, and A.

In a further embodiment of the first propeptide $X_5$ is selected from R, Q, K, G, H, S, and P.

In a further embodiment of the first propeptide $X_6$ is selected from E, R, and Q.

In a further embodiment of the first propeptide $X_7$ is selected from Q, N, E, K, and R.

In a further embodiment of the first propeptide $X_8$ is selected from A and G.

In a further embodiment of the first propeptide $X_9$ is selected from N, H, S, and R.

In a further embodiment of the first propeptide $X_{10}$ is selected from Q, N, T, G, S, K, and E.

In a further embodiment of the first propeptide $X_{11}$ is selected from V, I, F, and L.

In a further embodiment of the first propeptide $X_{12}$ is selected from L, I, and V.

In a further embodiment of the first propeptide $X_{13}$ is selected from Q, A, S, H, V, K, N, and R.

In a further embodiment of the first propeptide $X_{14}$ is selected from R, H, K, I, and P, or is absent.

In a further embodiment of the first propeptide $X_{15}$ is selected from R, H, K, Q, V, Y, P, A, T, W, and L, or is absent.

In a further embodiment of the first propeptide $X_{16}$ is selected from R, H, T, Q, K, Y, and P, or is absent.

In a further embodiment of the first propeptide $X_{17}$ is selected from R, H, and K, or is absent.

In a further embodiment of the first propeptide $X_{17}$ is R.

In the present specification, amino acid residues are represented using abbreviations, as indicated in table 1, approved by IUPAC-IUB Commission on Biochemical Nomenclature (CBN). With respect to amino acids and the like having isomers, those which are represented by the following abbreviations are in natural L-form. Further, the left and right ends of an amino acid sequence of a peptide are, respectively, the N- and C-termini unless otherwise specified.

In a further embodiment of the invention the first propeptide comprises an amino acid sequence with an inhibition constant (Ki) less than 1 mM. In a further embodiment the amino acid sequence has a Ki of less than 0.5 mM. In a still further embodiment the amino acid sequence has a Ki between 0.1 nM and 0.5 mM.

In a further embodiment of the invention the first propeptide comprises an amino acid sequence with at least 30% homology to a sequence independently selected from the group consisting of SEQ ID NO:1, 2, 3, 4, 5, 6, 7, 8, 9, 10, 11, 12, 13, 14, 15, 16, 17 and 18.

In a further embodiment the first propeptide comprises an amino acid sequence with at least 40% homology to a sequence independently selected from the group consisting of SEQ ID NO:1, 2, 3, 4, 5, 6, 7, 8, 9, 10, 11, 12, 13, 14, 15, 16, 17 and 18.

In a further embodiment the first propeptide comprises an amino acid sequence with at least 50% homology to a sequence independently selected from the group consisting of SEQ ID NO:1, 2, 3, 4, 5, 6, 7, 8, 9, 10, 11, 12, 13, 14, 15, 16, 17 and 18.

In a further embodiment of the invention the first propeptide comprises an amino acid sequence with a Ki less than 1 mM and with at least 30% homology to a sequence independently selected from the group consisting of SEQ ID NO:1, 2, 3, 4, 5, 6, 7, 8, 9, 10, 11, 12, 13, 14, 15, 16, 17 and 18.

In a further embodiment of the invention the first propeptide comprises a specific amino acid sequence independently selected from the group consisting of SEQ ID NO:1, 2, 3, 4, 5, 6, 7, 8, 9, 10, 11, 12, 13, 14, 15, 16, 17 and 18.

In a further embodiment of the invention the second free propeptide comprises an amino acid sequence of the formula:

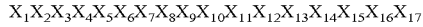

$$X_1X_2X_3X_4X_5X_6X_7X_8X_9X_{10}X_{11}X_{12}X_{13}X_{14}X_{15}X_{16}X_{17}$$

Wherein $X_1$, $X_4$, $X_5$, $X_6$, $X_7$, $X_9$, $X_{10}$ and $X_{13}$, are independently selected from
G, P, A, V, L, I, M, C, F, Y, W, H, K, R, Q, N, E, D, S, and T
and wherein $X_2$, $X_3$, $X_{11}$ and $X_{12}$ are independently selected from
V, L, P, N, A, I, S, F, M, W, Q, T, and Y
and wherein $X_8$ is independently selected from
G, and A
and wherein $X_{14}$, $X_{15}$, $X_{16}$ and $X_{17}$ are independently selected from
R, H, A, T, W, L, I, V, Q, K, Y, P, or is absent.

In one embodiment of the second free propeptide $X_1$ is selected from A, S, N, R, T, and H.

In a further embodiment of the second free propeptide $X_2$ is selected from V, L, P, N, and A.

In a further embodiment of the second free propeptide $X_3$ is selected from L, I, V, and S.

In a further embodiment of the second free propeptide $X_4$ is selected from S, R, N, T, D, and A.

In a further embodiment of the second free propeptide $X_5$ is selected from R, Q, K, G, H, S, and P.

In a further embodiment of the second free propeptide $X_6$ is selected from E, R, and Q.

In a further embodiment of the second free propeptide $X_7$ is selected from Q, N, E, K, and R.

In a further embodiment of the second free propeptide $X_8$ is selected from A and G.

In a further embodiment of the second free propeptide $X_9$ is selected from N, H, S, and R.

In a further embodiment of the second free propeptide $X_{10}$ is selected from Q, N, T, G, S, K, and E.

In a further embodiment of the second free propeptide $X_{11}$ is selected from V, I, F, and L.

In a further embodiment of the second free propeptide $X_{12}$ is selected from L, I, and V.

In a further embodiment of the second free propeptide $X_{13}$ is selected from Q, A, S, H, V, K, N, and R.

In a further embodiment of the second free propeptide $X_{14}$ is selected from R, H, K, I, and P, or is absent.

In a further embodiment of the second free propeptide $X_{15}$ is selected from R, H, K, Q, V, Y, P, A, T, W, and L, or is absent.

In a further embodiment of the second free propeptide $X_{16}$ is selected from R, H, T, Q, K, Y, and P, or is absent.

In a further embodiment of the second free propeptid $X_{17}$ is selected from R, H, T, Q, K, Y, and P, or is absent.

In a further embodiment of the invention the second free propeptide comprises an amino acid sequence with a Ki less than 1 mM. In a further embodiment the amino acid sequence has a Ki of less than 0.5 mM. In a still further embodiment the amino acid sequence has a Ki between 0.1 nM and 0.5 mM.

In a further embodiment of the invention the second propeptide comprises an amino acid sequence with at least 30% homology to a sequence independently selected from the group consisting of SEQ ID NO:1, 2, 3, 4, 5, 6, 7, 8, 9, 10, 11, 12, 13, 14, 15, 16, 17 and 18.

In a further embodiment the second propeptide comprises an amino acid sequence with at least 40% homology to a sequence independently selected from the group consisting of SEQ ID NO:1, 2, 3, 4, 5, 6, 7, 8, 9, 10, 11, 12, 13, 14, 15, 16, 17 and 18.

In a further embodiment the second propeptide comprises an amino acid sequence with at least 50% homology to a sequence independently selected from the group consisting of SEQ ID NO:1, 2, 3, 4, 5, 6, 7, 8, 9, 10, 11, 12, 13, 14, 15, 16, 17 and 18.

In a further embodiment of the invention the second free propeptide comprises an amino acid sequence with a Ki less than 1 mM and with at least 30% homology to a specific sequence independently selected from the group consisting of SEQ ID NO:1, 2, 3, 4, 5, 6, 7, 8, 9, 10, 11, 12, 13, 14, 15, 16, 17 and 18.

In a further embodiment of the invention the second free propeptide comprises a specific amino acid sequence independently selected from the group consisting of SEQ ID NO:1, 2, 3, 4, 5, 6, 7, 8, 9, 10, 11, 12, 13, 14, 15, 16, 17 and 18.

In a further embodiment of the invention the eucaryotic host cell is a yeast cell.

In a further embodiment of the invention the eucaryotic host cell is an insect cell.

In a further embodiment of the invention the eucaryotic host cell is a mammalian cell.

In a further embodiment of the invention the eucaryotic host cell is a human cell.

In a further embodiment of the invention the eucaryotic host cell is independently selected from BHK cells, HEK cells, COS cells or CHO cells.

In a further embodiment of the invention the first polynucleotide is DNA.

In a further embodiment of the invention the second polynucleotide is DNA.

In a further embodiment of the invention the first polynucleotide is RNA.

In a further embodiment of the invention the second polynucleotide is RNA.

In a further embodiment of the invention the first expression unit is present on a first vector and the second expression unit is present on a second separate vector.

In a further embodiment of the invention the first expression unit and the second expression unit are present on the same vector.

In a further embodiment of the invention the first vector is a plasmid vector.

In a further embodiment of the invention the second vector is a plasmid vector.

In a further embodiment of the invention the first vector is a phage vector.

In a further embodiment of the invention the second vector is a phage vector.

In a further embodiment of the invention the culture medium is a serum free medium.

In a further embodiment of the invention the first polynucleotide is plasmid DNA.

In a further embodiment of the invention the second polynucleotide is plasmid DNA.

The term "binding sequence for a gamma-glutamyl carboxylase" as used herein means the nessesary amino acid residues within a sequence (i.e. recognition sequence) for binding or docking or interaction with a gamma-glutamyl carboxylase.

In a further embodiment of the invention the first propeptide has a higher affinity (as measured by the inhibition constant ($K_i$)) for the carboxylase than the second free propeptide. Provided there are two separable functions of the propeptides of vitamin K-dependent proteins on the carboxylase, substrate binding and activity regulation, different affinities and concentrations of the covalently attached propeptide and of the free propeptide might influence the overall capacity of a producer cell to carboxylate recombinant vitamin K-dependent protein. Co-expression of free propeptide and covalently attached propeptide, and combinations thereof might increase the production of functional recombinant FVII (rFVII). In order not to inhibit the carboxylation of the newly synthesized Glu-containing vitamin K-dependent protein it is preferred that the second free propeptide has a lower affinity than the propeptide covalently attached to the vitamin K-dependent protein to be gamma-carboxylated.

$K_i$ for free propeptides are determined according to Stanley et al (Biochemistry, 38, 15681-15687(1999) and J. Biol. Chem. 274, 16940-16944.)

In a further embodiment the free propeptides to be co-expressed with the vitamin K-dependent protein are preferably selected from the lists as summarized in table 2 and 3. Specifically, table 2 contains the following propeptide sequences: 1) Consensus sequence (SEQ ID NO: 1); 2) Factor X (SEQ ID NO:2); 3) Matrix Gla Protein (SEQ ID NO:3); 4) FVII (SEQ ID NO:7); 5) Protein S (SEQ ID NO:4); 6) PRGP1 (SEQ ID NO:5); 7) Factor IX (SEQ ID NO:8); 8) Protein C (SEQ ID NO:9); 9) Prothrombin (SEQ ID NO:6); and 10) Osteocalcin (SEQ ID NO:21). Table 3 contains the following propeptide sequences: a) authentic—1) FVII (SEQ ID NO:7), 2) Factor IX (SEQ ID NO:8), and 3) Protein C (SEQ ID NO:9); b) mutants—1) Osteocalcin (G-10A, V-6L) (SEQ ID NO:10), 2) FVII (A-10G) (SEQ ID NO:11), 3) FVII (H-9R) (SEQ ID NO:12), 4) FVII (H-9K) (SEQ ID NO:13), 5) FVII (H-9L) (SEQ ID NO:14), and 6) FVII (V-15S) (SEQ ID NO:15); and c) truncated—1) FVII (SEQ ID NO:16), 2) Factor IX (SEQ ID NO:17), and 3) Protein C (SEQ ID NO:18).

TABLE 1

Abbreviations for amino acid residues:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| isoleucine Ile | I | |
| Methionine Met | M | |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

TABLE 2

Amino acid sequence of propeptides from Vitamin K-dependent proteins and consensus propeptide

| Position minus | 18 | 17 | 16 | 15 | 14 | 13 | 12 | 11 | 10 | 9 | 8 | 7 | 6 | 5 | 4 | 3 | 2 | 1 | *Ki nM |
|---|---|---|---|---|---|---|---|---|---|---|---|---|---|---|---|---|---|---|---|
| Consensus* | A | V | F | L | S | R | E | Q | A | N | Q | V | L | Q | R | R | R | R | 0,43 |
| factor X | S | L | F | I | R | R | E | Q | A | N | N | I | L | A | R | V | T | R | 2,6 |
| Matrix Gla Protein | N | P | F | I | N | R | R | N | A | N | T | F | I | S | P | Q | Q | R | 5,8 |
| FVII | A | V | F | V | T | Q | E | E | A | H | G | V | L | H | R | R | R | R | 11,1 |
| Protein S | A | N | F | L | S | K | Q | Q | A | S | Q | V | L | V | R | K | R | R | 12,2 |

TABLE 2-continued

Amino acid sequence of propeptides from Vitamin K-dependent proteins and consensus propeptide

| Position minus | 18 | 17 | 16 | 15 | 14 | 13 | 12 | 11 | 10 | 9 | 8 | 7 | 6 | 5 | 4 | 3 | 2 | 1 | *Ki nM |
|---|---|---|---|---|---|---|---|---|---|---|---|---|---|---|---|---|---|---|---|
| PRGP1 | R | V | F | L | T | G | E | K | A | N | S | I | L | K | R | Y | P | R | 12,8 |
| factor IX | T | V | F | L | D | H | E | N | A | N | K | I | L | N | R | P | K | R | 33,6 |
| Protein C | S | V | F | S | S | S | E | R | A | H | Q | V | L | R | I | R | K | R | 230 |
| Prothrombin | H | V | F | L | A | P | Q | Q | A | R | S | L | L | Q | R | V | R | R | 277 |
| Osteocalcin | A | A | F | V | S | K | Q | E | G | S | E | V | V | K | R | P | R | R | >500,000 |

*Stanley et al (1999) Biochemistry, 38, 15681-15687 and J.Biol.Chem. 274, 16940-16944

Table 3: Examples of free propeptides to be co-expressed with a vitamin K-dependent protein

| | Position minus | 18 | 17 | 16 | 15 | 14 | 13 | 12 | 11 | 10 | 9 | 8 | 7 | 6 | 5 | 4 | 3 | 2 | 1 |
|---|---|---|---|---|---|---|---|---|---|---|---|---|---|---|---|---|---|---|---|
| Authentic | FVII | A | V | F | V | T | Q | E | E | A | H | G | V | L | H | R | R | R | R |
| | factor IX | T | V | F | L | D | H | E | N | A | N | K | I | L | N | R | P | K | R |
| | Protein C | S | V | F | S | S | S | E | R | A | H | Q | V | L | R | I | R | K | R |
| Mutants | Osteocalcin(G-10A, V-6L) | A | A | F | V | S | K | Q | E | A | S | E | V | L | K | R | P | R | R |
| | FVII (A-10G) | A | V | F | V | T | Q | E | E | G | H | G | V | L | H | R | R | R | R |
| | FVII (H-9R) | A | V | F | V | T | Q | E | E | A | R | G | V | L | H | R | R | R | R |
| | FVII (H-9K) | A | V | F | V | T | Q | E | E | A | K | G | V | L | H | R | R | R | R |
| | FVII (H-9L) | A | V | F | V | T | Q | E | E | A | L | G | V | L | H | R | R | R | R |
| | FVII (V-15S) | A | V | F | S | T | Q | E | E | A | H | G | V | L | H | R | R | R | R |
| Truncated | FVII | A | V | F | V | T | Q | E | E | A | H | G | V | L | H | | | | |
| | factor IX | T | V | F | L | D | H | E | N | A | N | K | I | L | N | | | | |
| | Protein C | S | V | F | S | S | S | E | R | A | H | Q | V | L | R | | | | |

The invention also relates to a method of preparing vitamin K-dependent proteins as mentioned above. The vitamin K-dependent proteins are preferably produced by recombinant DNA techniques. To this end, DNA sequences encoding the vitamin K-dependent proteins may be isolated by preparing a genomic or cDNA library and screening for DNA sequences coding for all or part of the protein by hybridization using synthetic oligonucleotide probes in accordance with standard techniques (cf. Sambrook et al., *Molecular Cloning: A Laboratory Manual*, Cold Spring Harbor Laboratory, Cold Spring Harbor, N.Y., 1989). For the present purpose, the DNA sequence encoding the protein is preferably of human origin, i.e. derived from a human genomic DNA or cDNA library.

The invention also relates to a method of activating (i.e., turning on) a gene encoding a vitamin K-dependent protein present in primary, secondary, or immortalized cells of vertebrate origin, which is normally not expressed in the cells or is not expressed at physiologically significant levels in the cells as obtained. Homologous recombination can be used to replace or disable the regulatory region normally associated with the gene in cells as obtained with a regulatory sequence which causes the gene to be expressed at levels higher than evident in the corresponding nontransfected cell, or to display a pattern of regulation or induction that is different than evident in the corresponding nontransfected cell. The invention, therefore, also relates to a method of preparing vitamin K-dependent proteins by turning on or activating an endogenous gene which encodes the vitamin K-dependent protein in transfected primary, secondary, or immortalized cells. Activation of endogenous genes may be performed as described in U.S. Pat. No. 5,968,502 The DNA sequences encoding the vitamin K-dependent proteins may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. According to the phosphoamidite method, oligonucleotides are synthesized, e.g. in an automatic DNA synthesizer, purified, annealed, ligated and cloned in suitable vectors.

The DNA sequences may also be prepared by polymerase chain reaction using specific primers, for instance as described in U.S. Pat. No. 4,683,202, Saiki et al., *Science* 239 (1988), 487-491, or Sambrook et al., supra.

The DNA sequences encoding the vitamin K-dependent proteins are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the vitamin K-dependent proteins is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

The promoter may be any DNA sequence, which shows transcriptional activity in the host cell of choice and may be derived from genes encoding proteins either homologous or heterologous to the host cell.

Examples of suitable promoters for directing the transcription of the DNA encoding the vitamin K-dependent protein in mammalian cells are the SV40 promoter (Subramani et al., *Mol. Cell Biol.* 1 (1981), 854-864), the MT-1 (metallothionein gene) promoter (Palmiter et al., *Science* 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

An example of a suitable promoter for use in insect cells is the polyhedrin promoter (U.S. Pat. No. 4,745,051; Vasuvedan et al., *FEBS Lett.* 311, (1992) 7-11), the P10 promoter (J. M. Vlak et al., *J. Gen. Virology* 69, 1988, pp. 765-776), the *Autographa californica* polyhedrosis virus basic protein promoter (EP 397 485), the baculovirus immediate early gene 1 promoter (U.S. Pat. Nos. 5,155,037; 5,162,222), or the baculovirus 39K delayed-early gene promoter (U.S. Pat. Nos. 5,155,037; 5,162,222).

Examples of suitable promoters for use in yeast host cells include promoters from yeast glycolytic genes (Hitzeman et al., *J. Biol. Chem.* 255 (1980), 12073-12080; Alber and Kawasaki, *J. Mol. Appl. Gen.* 1 (1982), 419-434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652-654) promoters.

Examples of suitable promoters for use in filamentous fungus host cells are, for instance, the ADH3 promoter (McKnight et al., *The EMBO J.* 4 (1985), 2093-2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the vitamin K-dependent proteins may also, if necessary, be operably connected to a suitable terminator, such as the human growth hormone terminator (Palmiter et al., *Science* 222, 1983, pp. 809-814) or the TPI1 (Alber and Kawasaki, *J. Mol. Appl. Gen.* 1, 1982, pp. 419-434) or ADH3 (McKnight et al., *The EMBO J.* 4, 1985, pp. 2093-2099) terminators. The vector may also contain a set of RNA splice sites located downstream from the promoter and upstream from the insertion site for the FVII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nuc. Acids Res. 9:3719-3730, 1981) or the polyadenylation signal from the human FVII gene or the bovine FVII gene. The expression vectors may also include a noncoding viral leader sequence, such as the adenovirus 2 tripartite leader, located between the promoter and the RNA splice sites; and enhancer sequences, such as the SV40 enhancer.

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2μ replication genes REP 1-3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125-130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD or sC.

To direct the vitamin K-dependent proteins of the present invention into the secretory pathway of the host cells, a secretory signal sequence (also known as a leader sequence, prepro sequence or pre sequence) may be provided in the recombinant vector. The secretory signal sequence is joined to the DNA sequences encoding the vitamin K-dependent proteins in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed vitamin K-dependent proteins into the secretory pathway of the cell. The signal peptide may be naturally occurring signal peptide, or a functional part thereof, or it may be a synthetic peptide. Suitable signal peptides have been found to be the α-factor signal peptide. (cf. U.S. Pat. No. 4,870,008), the signal peptide of mouse salivary amylase (cf. O. Hagenbuchle et al., *Nature* 289, 1981, pp. 643-646), a modified carboxypeptidase signal peptide (cf. L. A. Valls et al., *Cell* 48, 1987, pp. 887-897), the yeast BAR1 signal peptide (cf. WO 87/02670), or the yeast aspartic protease 3 (YAP3) signal peptide (cf. M. Egel-Mitani et al., *Yeast* 6, 1990, pp. 127-137).

For efficient secretion in yeast, a sequence encoding a leader peptide may also be inserted downstream of the signal sequence and upstream of the DNA sequence encoding the vitamin K-dependent proteins. The function of the leader peptide is to allow the expressed peptide to be directed from the endoplasmic reticulum to the Golgi apparatus and further to a secretory vesicle for secretion into the culture medium (i.e. exportation of the vitamin K-dependent proteins across the cell wall or at least through the cellular membrane into the periplasmic space of the yeast cell). The leader peptide may be the yeast x-factor leader (the use of which is described in e.g. U.S. Pat. Nos. 4,546,082, 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the vitamin K-dependent proteins, the promoter and optionally the terminator and/or secretory signal sequence, respectively, and to insert them into suitable vectors containing the information necessary for replication, are well known to persons skilled in the art (cf., for instance, Sambrook et al., *Molecular Cloning: A Laboratory Manual*, Cold Spring Harbor, N.Y., 1989).

Methods of transfecting mammalian cells and expressing DNA sequences introduced in the cells are described in e.g. Kaufman and Sharp, *J. Mol. Biol.* 159 (1982), 601-621; Southern and Berg, *J. Mol. Appl. Genet.* 1 (1982), 327-341; Loyter et al., *Proc. Natl. Acad. Sci. USA* 79 (1982), 422-426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841-845.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the vitamin K-dependent protein of interest. Media generally include a carbon source, a nitrogen source, essential amino acids, essential sugars, vitamins, salts, phospholipids, protein and growth factors. For production of gamma-carboxylated proteins, the medium will contain vitamin K, preferably at a concentration of about 0.1 μg/ml to about 5 μg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the vitamin K-dependent protein of interest.

The host cell into which the DNA sequences encoding the vitamin K-dependent proteins is introduced may be any cell, which is capable of producing the posttranslational modified vitamin K-dependent proteins and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., J. Gen. Virol. 36:59-72, 1977) cell lines. A preferred BHK cell line is the tk$^{-}$ts13 BHK cell line (Waechter and Baserga, Proc. Natl. Acad. Sci. USA 79:1106-1110, 1982, incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk$^{-}$ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, Proc. Natl. Acad. Sci. USA 77:4216-4220, 1980).

Examples of suitable yeasts cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous polypeptides there from are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the vitamin K-dependent proteins may be preceded by a signal sequence and optionally a leader sequence, e.g. as described above. Further examples of suitable yeast cells are strains of Kluyveromyces, such as *K. lactis*, Hansenula, e.g. *H. polymorpha*, or Pichia, e.g. *P. pastoris* (cf. Gleeson et al., *J. Gen. Microbiol.* 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae*, *A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, Gene 78: 147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. Nos. 4,745,051; 4,879,236; 5,155,037; 5,162,222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the vitamin K-dependent protein after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The vitamin K-dependent protein produced by the cells may then be recovered from the culture medium by conventional procedures including separating the host cells from the medium by centrifugation or filtration, precipitating the proteinaqueous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

For the preparation of recombinant human FVII or variants thereof, a cloned wild-type FVII DNA sequence is used. This sequence may be modified to encode the desired FVII protein or variants thereof. The sequence is then inserted into an expression vector, which is in turn transformed or transfected into host cells. Higher eucaryotic cells, in particular cultured mammalian cells, are preferred as host cells. The complete nucleotide and amino acid sequences for human FVII are known. See U.S. Pat. No. 4,784,950, which is incorporated herein by reference, where the cloning and expression of recombinant human FVII is described. The bovine FVII sequence is described in Takeya et al., J. Biol. Chem, 263: 14868-14872 (1988), which is incorporated by reference herein.

The amino acid sequence alterations may be accomplished by a variety of techniques. Modification of the DNA sequence may be by site-specific mutagenesis. Techniques for site-specific mutagenesis are well known in the art and are described by, for example, Zoller and Smith (DNA 3:479-488, 1984). Thus, using the nucleotide and amino acid sequences of FVII, one may introduce the alterations of choice.

DNA sequences for use within the present invention will typically encode a pre-pro peptide at the amino-terminus of the FVII protein to obtain proper post-translational processing (e.g. gamma-carboxylation of glutamic acid residues) and secretion from the host cell. The pre-pro peptide may be that of FVII or another vitamin K-dependent plasma protein, such as factor IX, factor X, prothrombin, protein C or protein S. As will be appreciated by those skilled in the art, additional modifications can be made in the amino acid sequence of FVII where those modifications do not significantly impair the ability of the protein to act as a coagulation factor. For example, FVII in the catalytic triad can also be modified in the activation cleavage site to inhibit the conversion of zymogen FVII into its activated two-chain form, as generally described in U.S. Pat. No. 5,288,629, incorporated herein by reference.

Within the present invention, transgenic animal technology may be employed to produce the vitamin K-dependent protein. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (typically from about 1 to 15 g/l). From a commercial point of view, it is clearly preferable to use as the host a species that has a large milk yield. While smaller animals such as mice and rats can be used (and are preferred at the proof of principle stage), within the present invention it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WIPO Publication WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489, incorporated herein by reference), beta-lactoglobulin, a-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as about 4.25 kbp DNA segment encompassing the 5' flanking promoter and non-coding portion of the beta-lactoglobulin gene. See Whitelaw et al., Biochem J. 286: 31-39 (1992). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836-840 (1988); Palmiter et al., Proc. Natl. Acad. Sci. USA 88: 478-482 (1991); Whitelaw et al., Transgenic Res. 1: 3-13 (1991); WO 89/01343; and WO 91/02318, each of which is incorporated herein by reference). In this regard, it is generally preferred, wher possible, to use genomic sequences containing all or some of the native introns of a gene encoding the protein or polypeptide of interest, thus the further inclusion of at least some introns from, e.g., the beta-lactoglobulin gene, is preferred. One such region is a DNA segment which provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the sequence encoding the vitamin K-dependent protein is replaced with corresponding sequences from a milk specific protein gene. Such replacement provides a putative tissue-specific initiation environment to enhance expression. It is convenient to replace the entire pre-pro sequence of the vitamin K-dependent protein and 5' non-coding sequences with those of, for example, the BLG gene, although smaller regions may be replaced.

For expression of a vitamin K-dependent protein in transgenic animals, a DNA segment encoding the vitamin K-dependent protein is operably linked to additional DNA segments required for its expression to produce expression units. Such additional segments include the above-mentioned promoter, as well as sequences which provide for termination of transcription and polyadenylation of mRNA. The expression units will further include a DNA segment encoding a secretory signal sequence operably linked to the segment encoding the vitamin K-dependent protein. The secretory signal sequence may be a native secretory signal sequence of the vitamin K-dependent protein or may be that of another protein, such as a milk protein. See, for example, von Heinje, Nuc. Acids Res. 14: 4683-4690 (1986); and Meade et al., U.S. Pat. No. 4,873,316, which are incorporated herein by reference.

Construction of expression units for use in transgenic animals is conveniently carried out by inserting a sequence encoding the vitamin K-dependent protein into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of the vitamin K-dependent protein, thereby creating a gene fusion that includes the expression control sequences of the milk protein gene. In any event, cloning of the expression units in plasmids or other vectors facilitates the amplification of the vitamin K-dependent protein. Amplification is conveniently carried out in bacterial (e.g. E. coli) host cells, thus the vectors will typically include an origin of replication and a selectable marker functional in bacterial host cells.

The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, Science 240: 1468-1474 (1988)) or site-directed integration using embryonic stem (ES) cells (reviewed by Bradley et al., Bio/Technology 10: 534-539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds.

General procedures for producing transgenic animals are known in the art. See, for example, Hogan et al., Manipulating the Mouse Embryo: A Laboratory Manual, Cold Spring Harbor Laboratory, 1986; Simons et al., Bio/Technology 6: 179-183 (1988); Wall et al., Biol. Reprod. 32: 645-651 (1985); Buhler et al., Bio/Technology 8: 140-143 (1990); Ebert et al., Bio/Technology 9: 835-838 (1991); Krimpenfort et al., Bio/Technology 9: 844-847 (1991); Wall et al., J. Cell. Biochem. 49: 113-120 (1992); U.S. Pat. Nos. 4,873,191 and 4,873,316; WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., Proc. Natl. Acad. Sci. USA 77: 7380-7384 (1980); Gordon and Ruddle, Science 214: 1244-1246 (1981); Palmiter and Brinster, Cell 41: 343-345 (1985); Brinster et al., Proc. Natl. Acad. Sci. USA 82: 4438-4442 (1985); and Hogan et al. (ibid.). These techniques were subsequently adapted for use with larger animals, including livestock species (see e.g., WIPO publications WO 88/00239, WO 90/05188, and WO 92/11757; and Simons et al., Bio/Technology 6: 179-183 (1988). To summarize, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed. Production in transgenic plants may also be employed. Expression may be generalized or directed to a particular organ, such as a tuber. See, Hiatt, Nature 344:469-479 (1990); Edelbaum et al., J. Interferon Res. 12:449-453 (1992); Sijmons et al., Bio/Technology 8:217-221 (1990); and European Patent Office Publication EP 255,378.

FVII produced according to the present invention may be purified by affinity chromatography on an anti-FVII antibody column. It is preferred that the immunoadsorption column comprise a high-specificity monoclonal antibody. The use of calcium-dependent monoclonal antibodies, as described by Wakabayashi et al., J. Biol. Chem, 261:11097-11108, (1986) and Thim et al., Biochem. 27: 7785-7793, (1988), incorporated by reference herein, is particularly preferred. Additional purification may be achieved by conventional chemical purification means, such as high performance liquid chromatography. Other methods of purification, including barium citrate precipitation, are known in the art, and may be applied to the purification of the FVII d scribed herein (see, generally, Scopes, R., Protein Purification, Springer-Verlag, N.Y., 1982). Substantially pure FVII of at least about 90 to 95% homogeneity is preferred, and 98 to 99% or more homogeneity most preferred, for pharmaceutical uses. Once purified, partially or to homogeneity as desired, the FVII may then be used therapeutically.

Conversion of single-chain FVII to active two-chain FVIIa may be achieved using factor XIIa as described by Hedner and Kisiel (1983, J. Clin. Invest. 71: 1836-1841), or with other proteases having trypsin-like specificity (Kisiel and Fujikawa, Behring Inst. Mitt. 73: 29-42, 1983). Alternatively FVII may be activated by passing it through an ion-exchange chromatography column, such as mono Q® (Pharmacia Fire Chemicals) or the like (Bjoern et al., 1986, Research Disclosures 269:564-565). The FVII molecules of the present invention and pharmaceutical compositions thereof are particularly useful for administration to humans to treat a variety of conditions involving intravascular coagulation.

Vitamin K-dependent proteins of the present invention can be used to treat certain types of hemophilia. Hemophilia A is characterized by the absence of active factor VIII, factor VIIIa, or the presence of inhibitors to factor VIII. Hemophilia B is characterized by the absence of active factor IX, factor IXa. FVII deficiency, although rare, responds well to factor VII administration (Bauer, K. A., 1996, Haemostasis, 26:155-158, suppl. 1). Factor VIII replacement therapy is limited due to development of high-titer inhibitory factor VIII antibodies in some patients. Alternatively, FVIIa can be used in the treatment of hemophilia A and B. Factor IXa and factor VIIIa activate factor X. Factor VIIa eliminates the need for factors IX and VIII by activating factor X directly, and can overcome the problems of factor IX and VIII deficiencies with few immunological consequences.

BRIEF DESCRIPTION OF THE DRAWINGS

The present invention is described in further detail in the examples with reference to the appended drawings wherein FIG. 1 The structure of correctly processed human coagulation FVII, amino acids 1 to 406, with gamma carboxylated Glu-residues (γ) and glycosylation (*). The arrow at amino acid residue 152 shows the site where single-chain FVII is cleaved to be converted to activated two-chain FVII (FVIIa).

Figure 1:
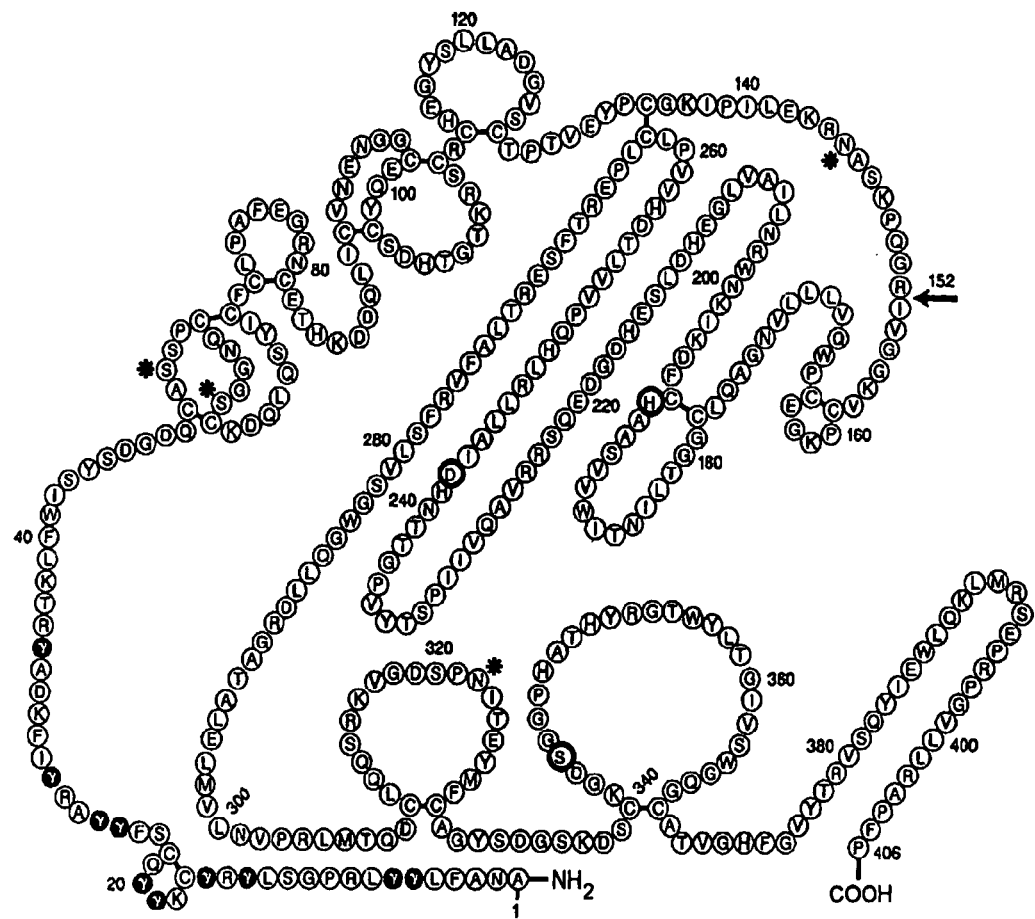
Figure 2:
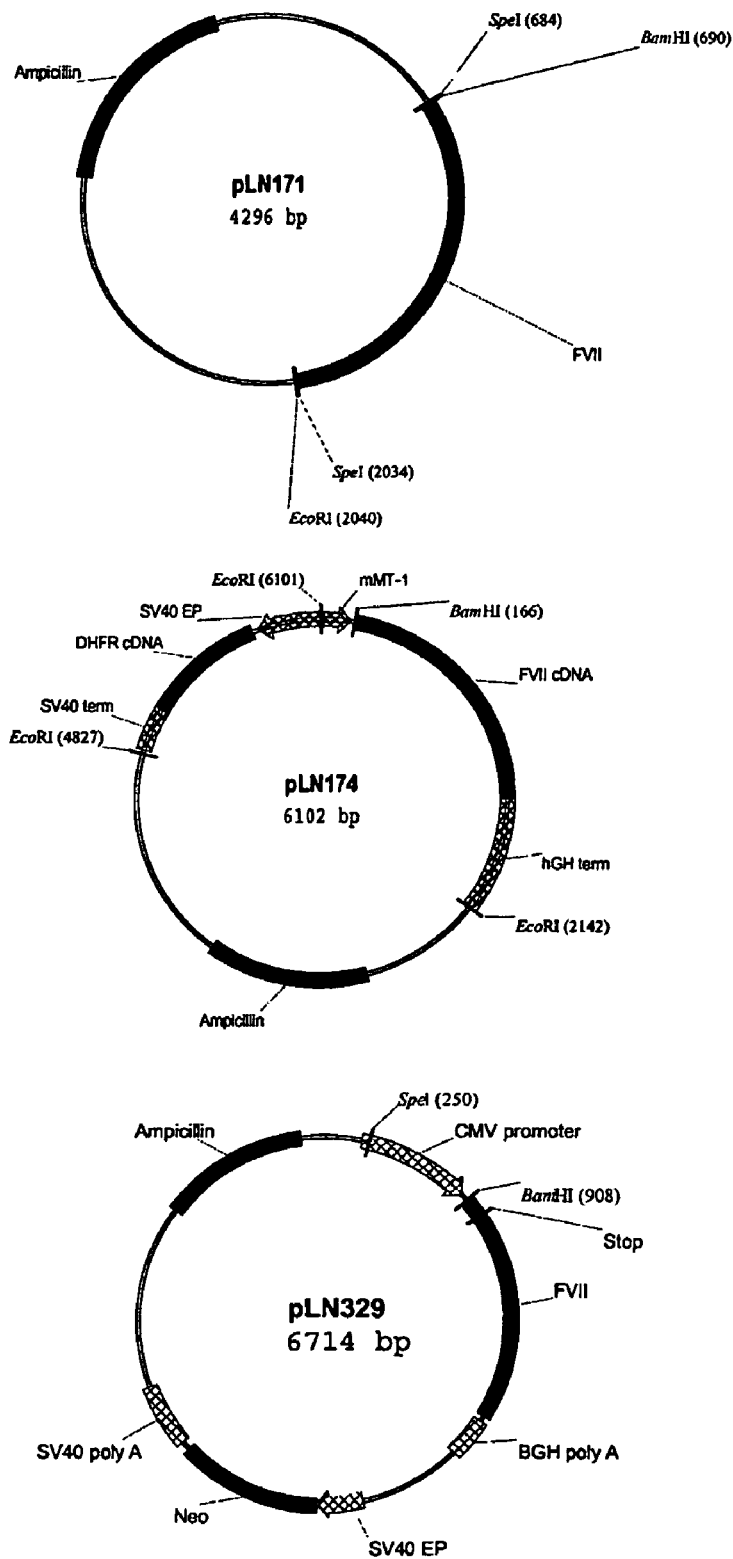
FIG. 2 Construction of plasmids for expression of free propeptides and for expression of recombinant human FVII with connected propeptide. Plasmids pLN171 and pLN174 express human FVII with connected propeptide naturally associated with FVII. Plasmid pLN329 has a stop codon inserted into the cDNA encoding FVII after the propeptide naturally associated with FVII to express only the free propeptide.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Example 1

Coexpression of FVII and the FVII Propeptide in CHO-K1 Cells

A plasmid vector pLN174 for expression of human FVII has been described (Persson and Nielsen. 1996. FEBS Lett. 385: 241-243). Briefly, it carries the cDNA nucleotide sequence encoding human FVII including the propeptide under the control of a mouse metallothionein promoter for transcription of the inserted cDNA, and mouse dihydrofolate reductase cDNA under the control of an SV40 early promoter for use as a selectable marker.

For construction of a plasmid vector encoding a gamma-carboxylation recognition sequence, a cloning vector pBluescript II KS+ (Stratagene) containing cDNA encoding FVII including its propeptide was used (pLN171). (Persson et al. 1997. J. Biol. Chem. 272: 19919-19924). A nucleotide sequence encoding a stop codon was inserted into the cDNA encoding FVII after the propeptide of FVII by inverse PCR-mediated mutagenesis on this cloning vector. The template plasmid was denatured by treatment with NaOH followed by PCR with Pwo (Boehringer-Mannheim) and Taq (Perkin-Elmer) polymerases with the following primers:

a) 5'-AGC GTT TTA GCG CCG GCG CCG GTG CAG GAC-3'      (SEQ ID NO:19)

b) 5'-CGC CGG CGC TAA AAC GCT TTC CTG GAG GAG CTG CGG CC-3'      (SEQ ID NO:20)

The resulting mix was digested with DpnI to digest residual template DNA and *Escherichia coli* were transformed with the PCR product. Clones were screened for the presence of the mutation by sequencing. The cDNA from a correct clone was transferred as a BamHI-EcoRI fragment to the expression plasmid pcDNA3 (Invitrogen). The resulting plasmid was termed pLN329.

CHO K1 cells (ATCC CCl61) were transfected with equal amounts of pLN174 and pLN329 with the Fugene6 method (Boehriner-Mannheim). Transfectants were selected by the addition of methotrexate to 1 µM and G-418 to 0.45 mg/ml. The pool of transfectants were cloned by limiting dilution and FVII expression from the clones was measured.

A high producing clone was further subcloned and a clone E11 with a specific FVII expression of 2.4 pg/cell/day in Dulbecco-modified Eagle's medium with 10% fetal calf serum was selected. The clone was adapted to serum free suspension culture in a commercially available CHO medium (JRH Bioscience).

The adapted cells were propagated sequentially in spinner cultures and as the cell number increased, the volume was gradually increased by addition of new medium.

After 25 days, 6 l of spinner culture were inoculated into a 50-liter bioreactor. The cells were propagated in the bioreactor and as the cell number increased, the volume was gradually increased by addition of new medium.

Finally, 50 l of seed culture were inoculated into a 500-liter production bioreactor containing macroporous Cytopore 1 carriers (Pharmacia), after which the suspension cells became immobilized in the carriers. The culture was maintained at 36° C. at a pH of 7.0-7.1 and a Dissolved Oxygen Tension (DOT) of 50% of saturation. The volume in the bioreactor was gradually increased by addition of new medium as the cell number increased. When the cell density reached approximately 10-12×105 cells/ml, the production phase was initiated and a medium change was performed every 24 hours: agitation was stopped to allow for sedimentation of the cell-containing carriers, and 80% of the culture supernatant was then harvested and replaced with new medium. The harvested culture supernatant was filtered to remove non-trapped cells (i.e. cells that were not immobilized in carriers) and cell debris and was then transferred for further processing.

During the production phas the cells reached $2-3 \times 10^7$ cells/ml and a titer of 8 mg factor VII/liter.

Example 2

Figure 3:
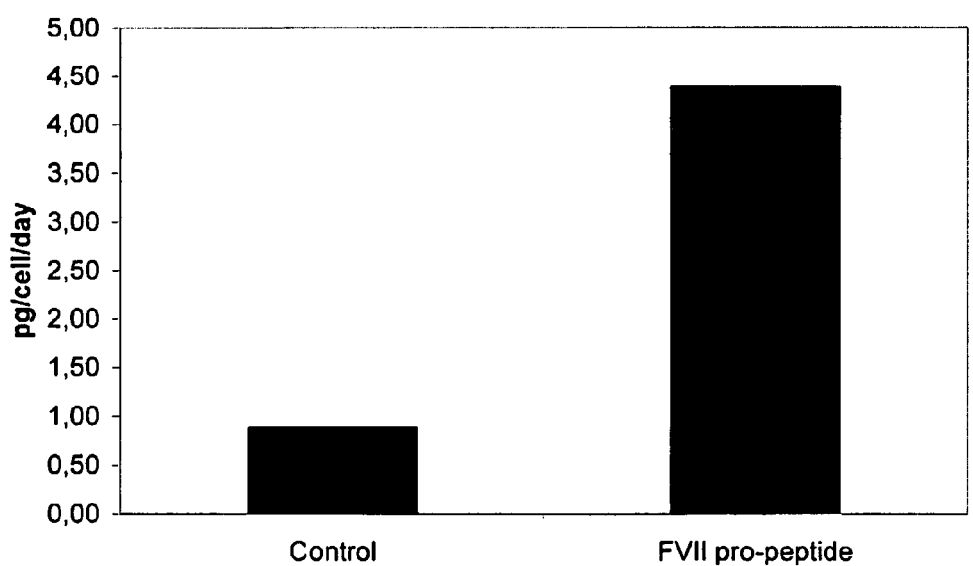
FIG. 3 Comparison of FVII expressing CHO-K1 cells (Control) and cells coexpressing FVII and a free FVII propeptide (FVII pro-peptide). Results are shown in pg FVII expression per cell per day.

Comparison of FVII Expressing CHO-K1 Cells and Cells Coexpressing FVII and a Free FVII Propeptide CHO-K1 cells were transfected with pLN174 and 1) empty pcDNA3.1+ vector or 2) FVII propeptide in pcDNA3.1+, as described in Example 1. Pools of transfectants were analysed for FVII expression and cell numbers. The FVII yields pr. cell pr. 24 hours are outlined in FIG. 3. The results show that coexpression of the FVII propeptide increases FVII yields pr. cell from approximately 1 pg/cell/day to 4 pg/cell/day. Results are shown in FIG. 3.

The invention claimed is:

1. An isolated eukaryotic host cell expressing: a) a first polynucleotide, said polynucleotide comprising a polynucleotide encoding a first propeptide and factor VII in a first expression unit, said first propeptide comprising an amino acid sequence selected from the group consisting of SEQ ID NO:1, 2, 3, 4, 5, 6, 7, 8, 9, 10, 11, 12, 13, 14, 15, 16, 17 and 18 and b) a second polynucleotide, said polynucleotide consisting of a polynucleotide encoding a second propeptide in a second expression unit, said second propeptide comprising an amino acid sequence selected from the group consisting of SEQ ID NO:1, 2, 3, 4, 5, 6, 7, 8, 9, 10, 11, 12, 13, 14, 15, 16, 17 and 18, and wherein said second polynucleotide only encodes the second propeptide.

2. The eukaryotic host cell according to claim 1, wherein said factor VII is human FVII.

3. The isolated eukaryotic host cell according to claim 1, wherein said host cell is transfected with a further polynucleotide encoding a gamma-glutamyl carboxylase in an expression unit.

4. The isolated eukaryotic host cell according to claim 1, wherein said host cell is a mammalian cell.

5. The isolated eukaryotic host cell according to claim 4, wherein said mammalian cell is a human cell.

6. The isolated eukaryotic host cell according to claim 4, wherein said mammalian cell is independently selected from BHK cells, HEK cells, COS cells, or CHO cells.

7. The isolated eukaryotic host cell according to claim 1, wherein said first and second polynucleotides are DNA.

8. The isolated eukaryotic host cell according to claim 1, wherein said first and second polynucleotides are RNA.

9. A method for producing factor VII comprising a) cultivation of a eukaryotic host cell according to claim 1 in a suitable culture medium under conditions which allow the first polynucleotide and the second polynucleotide to be expressed; and b) isolation of said factor VII from the medium.

10. The method according to claim 9, wherein said factor VII is human FVII.

11. The method according to claim 9, wherein said host cell is transfected with a further polynucleotide encoding a gamma-glutamyl carboxylase in an expression unit.

12. The method according to claim 9, wherein said first expression unit is present on a first vector and said second expression unit is present on a second separate vector.

13. The method according to claim 9, wherein said first expression unit and said second expression unit are present on the same vector.

14. The method according to claim 9, wherein said culture medium is a serum free medium.

15. The method according to claim 9, wherein said host cell is a mammalian cell.

16. The method according to claim 15, wherein said mammalian cell is a human cell.

17. The method according to claim 15, wherein said mammalian cell is independently selected from BHK cells, HEK cells, COS cells, or CHO cells.

18. The method according to claim 9, wherein said first and second polynucleotides are DNA.

19. The method according to claim 9, wherein said first and second polynucleotides are RNA.

20. A method for producing factor VIIa comprising a) cultivation of a eukaryotic host cell according to claim 1 in a suitable culture medium under conditions which allow the first polynucleotide and the second polynucleotide to be expressed; and b) isolation and activation of factor VII from the medium.

21. The method according to claim 20, wherein said factor VIIa is human factor VIIa.

22. The method according to claim 20, wherein said host cell is transfected with a further polynucleotide encoding a gamma-glutamyl carboxylase in an expression unit.

23. The method according to claim 20, wherein said first expression unit is present on a first vector and said second expression unit is present on a second separate vector.

24. The method according to claim 20, wherein said first expression unit and said second expression unit are present on the same vector.

25. The method according to claim 20, wherein said culture medium is a serum free medium.

26. The method according to claim 20, wherein said host cell is a mammalian cell.

27. The method according to claim 26, wherein said mammalian cell is a human cell.

28. The method according to claim 26, wherein said mammalian cell is independently selected from MIK cells, IIEK cells, COS cells, or CHO cells.

29. The method according to claim 20, wherein said first and second polynucleotides are DNA.

30. The method according to claim 20, wherein said first and second polynucleotides are RNA.

31. An isolated eukaryotic host cell transfected with: a) a first polynucleotide, said polynucleotide comprising a polynucleotide encoding a first propeptide and factor VII in a first expression unit, said first propeptide comprising an amino acid sequence selected from the group consisting of SEQ ID NO:1, 2, 3, 4, 5, 6, 7, 8, 9, 10, 11, 12, 13, 14, 15, 16, 17 and 18; and b) a second polynucleotide, said polynucleotide consisting of a polynucleotide encoding a second propeptide in a second expression unit, said second propeptide comprising an amino acid sequence selected from the group consisting of SEQ ID NO:1, 2, 3, 4, 5, 6, 7, 8, 9, 10, 11, 12, 13, 14, 15, 16, 17 and 18.

32. The eukaryotic host cell according to claim 31, wherein said factor VII is human FVII.

33. The isolated eukaryotic host cell according to claim 31, wherein said host cell is transfected with a further polynucleotide encoding a gamma-glutamyl carboxylase in an expression unit.

34. The isolated eukaryotic host cell according to claim 31, wherein said host cell is a mammalian cell.

35. The isolated eukaryotic host cell according to claim 34, wherein said mammalian cell is a human cell.

36. The isolated eukaryotic host cell according to claim 34, wherein said mammalian cell is independently selected from BHK cells, HEK cells, COS cells, or CHO cells.

37. The isolated eukaryotic host cell according to claim 31, wherein said first and second polynucleotides are DNA.

38. The isolated eukaryotic host cell according to claim 31, wherein said first and second polynucleotides are RNA.

39. A method for producing factor VII comprising a) transfection of a eukaryotic host cell with: i) a first polynucleotide, said polynucleotide comprising a polynucleotide encoding a first propeptide and factor VII in a first expression unit, said first propeptide comprising an amino acid sequence selected from the group consisting of SEQ ID NO:1, 2, 3, 4, 5, 6, 7, 8, 9, 10, 11, 12, 13, 14, 15, 16, 17 and 18 and ii) a second polynucleotide, said polynucleotide consisting of a polynucleotide encoding a second propeptide in a second expression unit, said second propeptide comprising an amino acid sequence selected from the group consisting of SEQ ID NO:1, 2, 3, 4, 5, 6, 7, 8, 9, 10, 11, 12, 13, 14, 15, 16, 17 and 18, to produce a co-transfected eukaryotic host cell; b) cultivation in a suitable culture medium of the co-transfected eukaryotic host cell under conditions which allow the first polynucleotide and the second polynucleotide to be expressed; and c) isolation of said factor VII from the medium.

40. The method according to claim 39, wherein said factor VII is human FVII.

41. The method according to claim 39, wherein said host cell is transfected with a further polynucleotide encoding a gamma-glutamyl carboxylase in an expression unit.

42. The method according to claim 39, wherein said first expression unit is present on a first vector and said second expression unit is present on a second separate vector.

43. The method according to claim 39, wherein said first expression unit and said second expression unit are present on the same vector.

44. The method according to claim 39, wherein said culture medium is a serum free medium.

45. The method according to claim 39, wherein said host cell is a mammalian cell.

46. The method according to claim 45, wherein said mammalian cell is a human cell.

47. The method according to claim 45, wherein said mammalian cell is independently selected from BHK cells, HEK cells, COS cells, or CHO cells.

48. The method according to claim 39, wherein said first and second polynucleotides are DNA.

49. The method according to claim 39, wherein said first and second polynucleotides are RNA.

50. A method for producing factor VIIa comprising a) transfection of a eukaryotic host cell with: i) a first polynucleotide, said polynucleotide comprising a polynucleotide encoding a first propeptide and factor VII in a first expression unit, said first propeptide comprising an amino acid sequence selected from the group consisting of SEQ ID NO:1, 2, 3, 4, 5, 6, 7, 8, 9, 10, 11, 12, 13, 14, 15, 16, 17 and 18 and ii) a second polynucleotide, said polynucleotide consisting of a polynucleotide encoding a second propeptide in a second expression unit, said second propeptide comprising an amino acid sequence selected from the group consisting of SEQ ID NO:1, 2, 3, 4, 5, 6, 7, 8, 9, 10, 11, 12, 13, 14, 15, 16, 17 and 18, to produce a co-transfected eukaryotic host cell; b) cultivation in a suitable culture medium of the co-transfected eukaryotic host cell under conditions which allow the first polynucleotide and the second polynucleotide to be expressed; and c) isolation and activation of said factor VII from the medium.

51. The method according to claim 50, wherein said factor VIIa is human FVIIa.

52. The method according to claim 50, wherein said host cell is transfected with a further polynucleotide encoding a gamma-glutamyl carboxylase in an expression unit.

53. The method according to claim 50, wherein said first expression unit is present on a first vector and said second expression unit is present on a second separate vector.

54. The method according to claim 50, wherein said first expression unit and said second expression unit are present on the same vector.

55. The method according to claim 50, wherein said culture medium is a serum free medium.

56. The method according to claim 50, wherein said host cell is a mammalian cell.

57. The method according to claim 56, wherein said mammalian cell is a human cell.

58. The method according to claim 56, wherein said mammalian cell is independently selected from BHK cells, HEK cells, COS cells, or CHO cells.

59. The method according to claim 56, wherein said first and second polynucleotides are DNA.

60. The method according to claim 50, wherein said first and second polynucleotides are RNA.

61. A recombinant vector, said vector comprising a first polynucleotide, said polynucleotide comprising a polynucleotide encoding a first propeptide and factor VII in a first expression unit, said first propeptide comprising an amino acid sequence selected from the group consisting of SEQ ID NO:1, 2, 3, 4, 5, 6, 7, 8, 9, 10, 11, 12, 13, 14, 15, 16, 17 and 18 and a second polynucleotide, said polynucleotide consisting of a polynucleotide encoding a second propeptide in a second expression unit, said second propeptide comprising an amino acid sequence selected from the group consisting of SEQ ID NO:1, 2, 3, 4, 5, 6, 7, 8, 9, 10, 11, 12, 13, 14, 15, 16, 17 and 18.

62. The recombinant vector according to claim 61, wherein said factor VII is human FVII.

63. The recombinant vector according to claim 61, wherein said first and second polynucleotides are DNA.

64. The recombinant vector according to claim 61, wherein said first and second polynucleotides are RNA.

65. A method for preparing a eukaryotic host cell producing factor VII, comprising transfection of a eukaryotic host cell with a vector of claim 61.

66. The method of claim 65, wherein said host cell is further transfected with a polynucleotide encoding a gamma-glutamyl carboxylase.

67. A method for preparing a eukaryotic host cell producing factor VII comprising a) transfection of a eukaryotic host cell with a first polynucleotide, said polynucleotide comprising a polynucleotide encoding a first propeptide and factor VII in a first expression unit, said first propeptide comprising an amino acid sequence selected from the group consisting of SEQ ID NO:1, 2, 3, 4, 5, 6, 7, 8, 9, 10, 11, 12, 13, 14, 15, 16, 17 and 18 and b) transfection with a second polynucleotide, said polynucleotide consisting of a polynucleotide encoding a second propeptide in a second expression unit, said second propeptide comprising an amino acid sequence selected from the group consisting of SEQ ID NO:1, 2, 3, 4, 5, 6, 7, 8, 9, 10, 11, 12, 13, 14, 15, 16, 17 and 18.

68. The method according to claim 67, wherein the said factor VII is human factor VII.

69. The method according to claim 67, wherein said host cell is further transfected with a polynucleotide encoding a gamma-glutamyl carboxylase.

* * * * *

UNITED STATES PATENT AND TRADEMARK OFFICE
CERTIFICATE OF CORRECTION

| | | |
|---|---|---|
| PATENT NO. | : 8,202,973 B2 | Page 1 of 1 |
| APPLICATION NO. | : 10/398422 | |
| DATED | : June 19, 2012 | |
| INVENTOR(S) | : Else M. Nicolaisen et al. | |

It is certified that error appears in the above-identified patent and that said Letters Patent is hereby corrected as shown below:

Column 37, claim number 28, line numbers 56-58, should read -- The method according to claim 26, wherein said mammalian cell is independently selected from BHK cells, HEK cells, COS cells, or CHO cells. --

Column 39, claim number 59, line number 36, "claim 56" should read -- claim 50. --

Signed and Sealed this
Twenty-seventh Day of November, 2012

David J. Kappos
*Director of the United States Patent and Trademark Office*

SEQUENCE LISTING

<160> NUMBER OF SEQ ID NOS: 21

<210> SEQ ID NO 1
<211> LENGTH: 18
<212> TYPE: PRT
<213> ORGANISM: Homo sapiens

<400> SEQUENCE: 1

Ala Val Phe Leu Ser Arg Glu Gln Ala Asn Gln Val Leu Gln Arg Arg
1               5                   10                  15

Arg Arg

<210> SEQ ID NO 2
<211> LENGTH: 18
<212> TYPE: PRT
<213> ORGANISM: Homo sapiens

<400> SEQUENCE: 2

Ser Leu Phe Ile Arg Arg Glu Gln Ala Asn Asn Ile Leu Ala Arg Val
1               5                   10                  15

Thr Arg

<210> SEQ ID NO 3
<211> LENGTH: 18
<212> TYPE: PRT
<213> ORGANISM: Homo sapiens

<400> SEQUENCE: 3

Asn Pro Phe Ile Asn Arg Arg Asn Ala Asn Thr Phe Ile Ser Pro Gln
1               5                   10                  15

Gln Arg

<210> SEQ ID NO 4
<211> LENGTH: 18
<212> TYPE: PRT
<213> ORGANISM: Homo sapiens

<400> SEQUENCE: 4

Ala Asn Phe Leu Ser Lys Gln Gln Ala Ser Gln Val Leu Val Arg Lys
1               5                   10                  15

Arg Arg

<210> SEQ ID NO 5
<211> LENGTH: 18
<212> TYPE: PRT
<213> ORGANISM: Homo sapiens

```
<400> SEQUENCE: 5

Arg Val Phe Leu Thr Gly Glu Lys Ala Asn Ser Ile Leu Lys Arg Tyr
1               5                   10                  15

Pro Arg

<210> SEQ ID NO 6
<211> LENGTH: 18
<212> TYPE: PRT
<213> ORGANISM: Homo sapiens

<400> SEQUENCE: 6

His Val Phe Leu Ala Pro Gln Gln Ala Arg Ser Leu Leu Gln Arg Val
1               5                   10                  15

Arg Arg

<210> SEQ ID NO 7
<211> LENGTH: 18
<212> TYPE: PRT
<213> ORGANISM: Homo sapiens

<400> SEQUENCE: 7

Ala Val Phe Val Thr Gln Glu Glu Ala His Gly Val Leu His Arg Arg
1               5                   10                  15

Arg Arg

<210> SEQ ID NO 8
<211> LENGTH: 18
<212> TYPE: PRT
<213> ORGANISM: Homo sapiens

<400> SEQUENCE: 8

Thr Val Phe Leu Asp His Glu Asn Ala Asn Lys Ile Leu Asn Arg Pro
1               5                   10                  15

Lys Arg

<210> SEQ ID NO 9
<211> LENGTH: 18
<212> TYPE: PRT
<213> ORGANISM: Homo sapiens

<400> SEQUENCE: 9

Ser Val Phe Ser Ser Glu Arg Ala His Gln Val Leu Arg Ile Arg
1               5                   10                  15

Lys Arg

<210> SEQ ID NO 10
<211> LENGTH: 18
<212> TYPE: PRT
<213> ORGANISM: Artificial
<220> FEATURE:
<223> OTHER INFORMATION: synthetic

<400> SEQUENCE: 10

Ala Ala Phe Val Ser Lys Gln Glu Ala Ser Glu Val Leu Lys Arg Pro
1               5                   10                  15

Arg Arg

<210> SEQ ID NO 11
<211> LENGTH: 18
<212> TYPE: PRT
<213> ORGANISM: Artificial
<220> FEATURE:
```

<223> OTHER INFORMATION: synthetic

<400> SEQUENCE: 11

Ala Val Phe Val Thr Gln Glu Glu Gly His Gly Val Leu His Arg Arg
1               5                   10                  15

Arg Arg

<210> SEQ ID NO 12
<211> LENGTH: 18
<212> TYPE: PRT
<213> ORGANISM: Artificial
<220> FEATURE:
<223> OTHER INFORMATION: synthetic

<400> SEQUENCE: 12

Ala Val Phe Val Thr Gln Glu Glu Ala Arg Gly Val Leu His Arg Arg
1               5                   10                  15

Arg Arg

<210> SEQ ID NO 13
<211> LENGTH: 18
<212> TYPE: PRT
<213> ORGANISM: Artificial
<220> FEATURE:
<223> OTHER INFORMATION: synthetic

<400> SEQUENCE: 13

Ala Val Phe Val Thr Gln Glu Glu Ala Lys Gly Val Leu His Arg Arg
1               5                   10                  15

Arg Arg

<210> SEQ ID NO 14
<211> LENGTH: 18
<212> TYPE: PRT
<213> ORGANISM: Artificial
<220> FEATURE:
<223> OTHER INFORMATION: synthetic

<400> SEQUENCE: 14

Ala Val Phe Val Thr Gln Glu Glu Ala Leu Gly Val Leu His Arg Arg
1               5                   10                  15

Arg Arg

<210> SEQ ID NO 15
<211> LENGTH: 18
<212> TYPE: PRT
<213> ORGANISM: Artificial
<220> FEATURE:
<223> OTHER INFORMATION: synthetic

<400> SEQUENCE: 15

Ala Val Phe Ser Thr Gln Glu Glu Ala His Gly Val Leu His Arg Arg
1               5                   10                  15

Arg Arg

<210> SEQ ID NO 16
<211> LENGTH: 14
<212> TYPE: PRT
<213> ORGANISM: Artificial
<220> FEATURE:
<223> OTHER INFORMATION: synthetic

<400> SEQUENCE: 16

Ala Val Phe Val Thr Gln Glu Glu Ala His Gly Val Leu His

```
                            1               5                    10

<210> SEQ ID NO 17
<211> LENGTH: 14
<212> TYPE: PRT
<213> ORGANISM: Homo sapiens

<400> SEQUENCE: 17

Thr Val Phe Leu Asp His Glu Asn Ala Asn Lys Ile Leu Asn
1               5                   10

<210> SEQ ID NO 18
<211> LENGTH: 14
<212> TYPE: PRT
<213> ORGANISM: Homo sapiens

<400> SEQUENCE: 18

Ser Val Phe Ser Ser Glu Arg Ala His Gln Val Leu Arg
1               5                   10

<210> SEQ ID NO 19
<211> LENGTH: 30
<212> TYPE: DNA
<213> ORGANISM: Artificial
<220> FEATURE:
<223> OTHER INFORMATION: synthetic

<400> SEQUENCE: 19
agcgttttag cgccggcgcc ggtgcaggac                                       30

<210> SEQ ID NO 20
<211> LENGTH: 38
<212> TYPE: DNA
<213> ORGANISM: Artificial
<220> FEATURE:
<223> OTHER INFORMATION: synthetic

<400> SEQUENCE: 20
cgccggcgct aaaacgcttt cctggaggag ctgcggcc                              38

<210> SEQ ID NO 21
<211> LENGTH: 18
<212> TYPE: PRT
<213> ORGANISM: Homo sapiens

<400> SEQUENCE: 21

Ala Ala Phe Val Ser Lys Gln Glu Gly Ser Glu Val Val Lys Arg Pro
1               5                   10                  15

Arg Arg
```